(12) United States Patent
Kobayashi et al.

(10) Patent No.: US 10,672,536 B2
(45) Date of Patent: Jun. 2, 2020

(54) BRAIDED CABLE AND METHOD OF IDENTIFYING BRAIDED BUNDLE IN BRAIDED CABLE

(71) Applicant: SANYO DENKO Co., Ltd., Kita-ku, Tokyo (JP)

(72) Inventors: Jun Kobayashi, Tokyo (JP); Hiroshi Sadanari, Tokyo (JP); Osamu Makino, Tokyo (JP)

(73) Assignee: SANYO DENKO CO., LTD., Kita-ku, Tokyo (JP)

( * ) Notice: Subject to any disclaimer, the term of this patent is extended or adjusted under 35 U.S.C. 154(b) by 0 days.

(21) Appl. No.: 16/304,923

(22) PCT Filed: Feb. 6, 2018

(86) PCT No.: PCT/JP2018/003919
§ 371 (c)(1),
(2) Date: Nov. 27, 2018

(87) PCT Pub. No.: WO2018/163689
PCT Pub. Date: Sep. 13, 2018

(65) Prior Publication Data
US 2019/0304627 A1  Oct. 3, 2019

(30) Foreign Application Priority Data

Mar. 7, 2017 (JP) ................................ 2017-042690

(51) Int. Cl.
*H01B 7/36* (2006.01)
*H01B 7/02* (2006.01)
(Continued)

(52) U.S. Cl.
CPC .......... *H01B 7/363* (2013.01); *H01B 7/0266* (2013.01); *H01B 7/36* (2013.01); *H01B 7/361* (2013.01); *H01B 11/02* (2013.01); *H02G 1/06* (2013.01)

(58) Field of Classification Search
None
See application file for complete search history.

(56) References Cited

U.S. PATENT DOCUMENTS 3,561,502 A * 2/1971 Swaisgood ............... B21F 7/00
                                                       140/115
3,605,068 A * 9/1971 Rayburn ................ H01R 13/28
                                                       439/291
(Continued)

FOREIGN PATENT DOCUMENTS

CN          1133477 A     10/1996
CN        201272547 Y      7/2009
(Continued)

OTHER PUBLICATIONS

FAQ_What_is_cable_lay_Eland_Cables. Eland Cables. (Year: 2018).*
(Continued)

*Primary Examiner* — Timothy J Thompson
*Assistant Examiner* — Muhammed Azam
(74) *Attorney, Agent, or Firm* — Flynn Thiel, P.C.

(57) ABSTRACT

A cable, which can serve as a mounting device for sensors, includes strands to be connected to the sensors. The strands are formed as a braided wire bundle. An insulating layer is provided on a surface of each of the strands in order to prevent mutual electric conduction of the strands. A particular braided bundle can be specified from among many braided bundles by using, as two indicators, a combination of colors of the insulating layers and a twist direction of the braided bundle.

5 Claims, 4 Drawing Sheets

(51) Int. Cl.
*H01B 11/02* (2006.01)
*H02G 1/06* (2006.01)

(56) References Cited

U.S. PATENT DOCUMENTS

| | | | | | |
|---|---|---|---|---|---|
| 3,797,217 | A | * | 3/1974 | Braun | D07B 7/02 57/294 |
| 3,965,558 | A | * | 6/1976 | McKee | H01R 43/01 29/749 |
| 4,128,736 | A | * | 12/1978 | Nutt | H01B 7/361 174/112 |
| 4,263,471 | A | * | 4/1981 | Bauguion | H01B 11/04 174/34 |
| 4,528,420 | A | * | 7/1985 | Kish | H01B 7/361 174/112 |
| 5,165,003 | A | * | 11/1992 | Carter | G02B 6/441 385/112 |
| 5,314,356 | A | * | 5/1994 | Isohata | H01R 13/6456 439/681 |
| 8,382,666 | B1 | * | 2/2013 | Mao | A61B 1/00121 600/202 |
| 2007/0251204 | A1 | * | 11/2007 | Susai | H01B 13/0006 57/9 |
| 2008/0142245 | A1 | * | 6/2008 | Cantz | H01B 7/16 174/111 |
| 2009/0011639 | A1 | * | 1/2009 | Ballard | H01B 9/003 439/607.01 |
| 2011/0069932 | A1 | * | 3/2011 | Overton | C03C 25/106 385/100 |
| 2012/0099825 | A1 | * | 4/2012 | Messer | G02B 6/4432 385/113 |
| 2015/0034354 | A1 | * | 2/2015 | Yoshida | B60R 16/0215 174/68.3 |
| 2019/0304627 | A1 | * | 10/2019 | Kobayashi | H01B 7/0266 |

FOREIGN PATENT DOCUMENTS

| | | |
|---|---|---|
| CN | 204178788 U | 2/2015 |
| GB | 403371 A | 12/1933 |
| JP | S57-109514 U | 7/1982 |
| JP | H6-5040 U | 1/1994 |
| JP | H8-138456 A | 5/1996 |
| JP | H09247829 A | 9/1997 |
| JP | H11-329103 A | 11/1999 |
| JP | 2002-253482 A | 9/2002 |
| JP | 2004158422 A | 6/2004 |
| JP | 2005-100756 A | 4/2005 |

OTHER PUBLICATIONS

International Search Report issued in Application No. PCT/JP2018/003919 dated Mar. 6, 2018 and English translation (5 pages).
Written Opinion issued in Application No. PCT/JP2018/003919 dated Mar. 6, 2018 (3 pages).
Office Action of Chinese Patent Office issued in corresponding Chinese Application No. 201880002226.1 dated Sep. 27, 2019 (7 pages).

* cited by examiner

FIG. 3

| Bobbin No. | Identification Wire | | Wiring Strands | |
|---|---|---|---|---|
| | Wire No. | | | |
| | 1 | 2 | 3 | 4 |
| S-1 | A | A | B | C |
| S-2 | A | A | B | D |
| S-3 | A | A | C | D |
| S-4 | B | B | C | D |
| S-5 | B | B | A | C |
| S-6 | B | B | A | D |
| S-7 | C | C | A | D |
| S-8 | C | C | B | D |
| S-9 | C | C | A | B |
| S-10 | D | D | A | B |
| S-11 | D | D | A | C |
| S-12 | D | D | B | C |
| Z-1 | D | D | B | C |
| Z-2 | D | D | A | C |
| Z-3 | D | D | A | B |
| Z-4 | C | C | A | B |
| Z-5 | C | C | B | D |
| Z-6 | C | C | A | D |
| Z-7 | B | B | A | D |
| Z-8 | B | B | A | C |
| Z-9 | B | B | C | D |
| Z-10 | A | A | C | D |
| Z-11 | A | A | B | D |
| Z-12 | A | A | B | A |

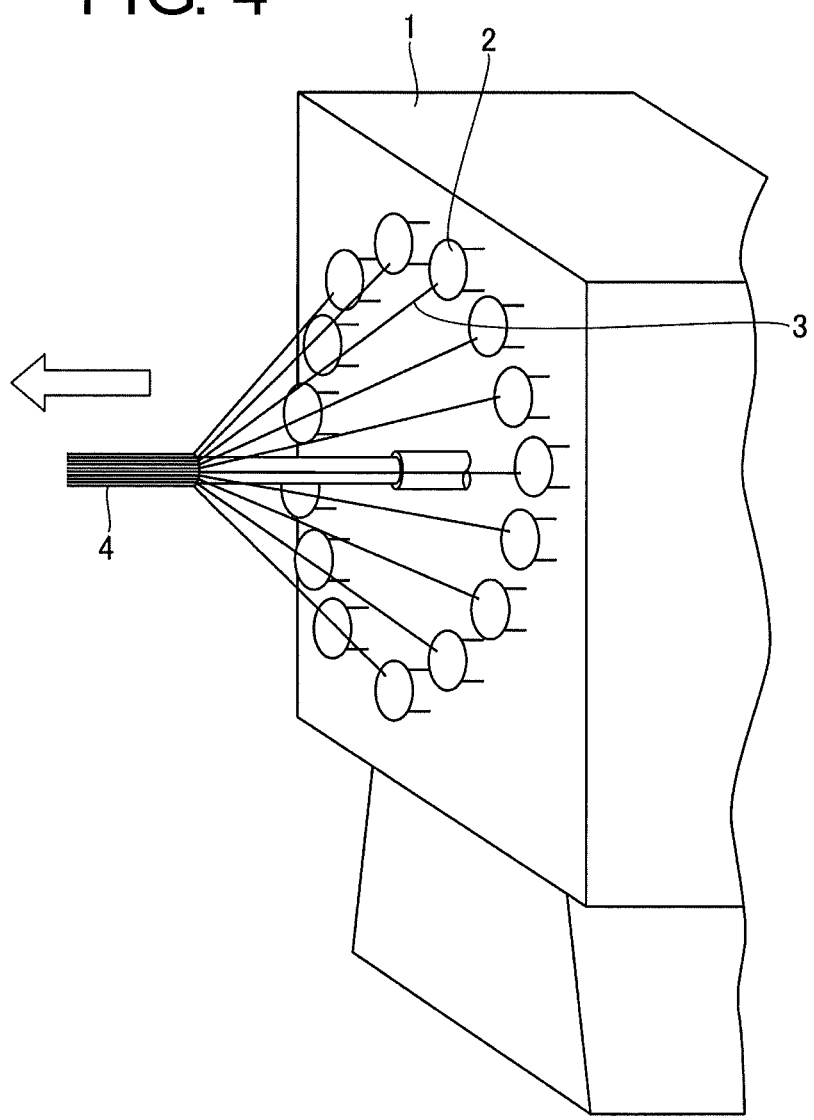

BRAIDED CABLE AND METHOD OF IDENTIFYING BRAIDED BUNDLE IN BRAIDED CABLE

TECHNICAL FIELD

The present invention relates to the technical field of temperature measurement, and in particular to the technical field of a temperature sensor-mounted cable including many temperature sensors in the cable.

BACKGROUND ART

In recent years, there has been a demand for making a more detailed temperature measurement in a certain space or region in various fields. For example, there have been a demand for finely measuring a particular region of the human body (for example, a temperature of the inner periphery of a tubular organ) during surgery or the like one the human body, and a demand for finely measuring a temperature in a certain space in a plastic greenhouse or the like. In such a case, measurements are made with a temperature sensor being placed on some sort of device such as a cable. As finer measurements are desired, a larger number of sensors need to be mounted inevitably.

When many sensors are installed using a cable as a device, the number of core wires for receiving signals from the sensors increases along with an increase in the number of the sensors. This leads to a larger finished diameter and poor flexibility. Moreover, there is a need to explicitly discriminate which core wire is connected to a sensor installed at which position. In this regard, an invention such that the identification is made on the basis of a combination of colors of core wire covering, and the like has been known as in the invention described in Japanese Utility Model Application Laid-Open No. Hei. 6-5040, for example.

SUMMARY OF THE INVENTION

Technical Problem

In an attempt to identify core wires with the technique described in Japanese Utility Model Application Laid-Open No. Hei. 6-5040 (Patent Literature 1), however, such a cable has a considerably large diameter and thus cannot be implemented on a practical level at all.

The inventor has changed the way of thinking without being bound to the conventional concept and has conceived an idea that the conventional problems can be solved by forming strands connected to sensors as a "braided wire." More specifically, a braided wire, which is typically disposed for the purpose of shielding (blocking) electromagnetic waves, for example, exhibits a shielding effect by the mutual electric conduction of strands. However, such electric conduction is removed by purposely insulating the strands from one another, and such strands are used as strands to be connected to many sensors.

By doing so, however, a problem arises such that identifying which one of the strands connects to a particular sensor from among the many braided strands becomes extremely difficult.

With regard to a braided wire, a plurality of strands are dispensed from bobbins 2, the dispensed strands are formed as a braided bundle 3, and the braided bundles 3 are braided by a braider 1 to produce a finished product (braided cable) 4, for example, as shown in FIG. 4. To control even the arrangement of the plurality of strands dispensed from the bobbins 2 is, at present, unrealistic in terms of its technical and cost aspects. However, it has been found out that identifying a particular braided bundle from among many braided bundles is sufficiently feasible by devising a color combination of the strands in each bobbin 2.

The present invention has been made to solve the problems described above. It is an object of the present invention to provide a cable having a sufficiently small diameter and excellent flexibility even when many sensors are mounted thereon.

Solution

To solve the aforementioned problems, the invention of the present application is a cable to be connected to sensors for receiving signals from the sensors, and is characterized in that strands to be connected to the sensors are formed as a braided wire, an insulating layer is provided on a surface of each of the strands in order to prevent mutual electric conduction of the strands, and a particular braided bundle can be specified from among many braided bundles using a combination of colors of the insulating layers and a twist direction of the braided bundle that constitutes the braided wire as two indicators.

Such a configuration enables the reliable provision of a sufficient number of strands enough to accommodate many sensors, and also allows the cable to have excellent flexibility specific to a braided wire. Furthermore, the braided wire has "twist directions." By additionally using such a "twist direction" as an indicator for identifying a braided bundle, the kinds of colors for the insulating layers can be reduced. This can achieve easy identification and cost reduction.

Further, the combination of the colors of the insulating layers is configured so that the same color is assigned to insulating layers in at least two strands of a plurality of strands that constitute the braided bundle, and colors of insulating layers in the other strands of the braided bundle are different from each other and the mutually-different colors are different from the color of the insulating layers in the two strands.

As just described, the identification of a braided bundle can be facilitated by assigning the same color to insulating layers in at least two of the strands that constitute the braided bundle. More specifically, many braided bundles can be narrowed down to a considerably smaller number of braided bundles by observing "what color two or more strands have in the braided bundle" in addition to its twist direction. The strands themselves are extremely thin wires, and a large number of such thin wires are braided to constitute a braided wire. Thus, when only a simple color combination is employed, it is difficult to identify even a braided bundle. However, by assigning the same color to at least two strands in a braided bundle, such a color becomes distinct in the braided bundle as a whole and can be thus identified easily.

The number of the strands that constitute the braided bundle is four, and the same color is assigned to insulating layers in two of the strands.

Even when the color combinations of the insulating layers include only four colors, such a configuration enables the identification of a considerable number of braided bundles as well as strands that constitute the braided bundles.

Moreover, the combination of the colors of the insulating layers for one twist direction is the same as that for the other twist direction.

Such a configuration can reduce the number of colors in the color combinations of the insulating layers, facilitate the identification, and thereby prevent identification errors from occurring.

From a different perspective, the present invention can be seen as an identification method of identifying, when many sensors are attached to a cable constituted by a plurality of strands, which one of the strands a particular one of the sensors corresponds to, and as a method of identifying a braided bundle in a braided cable, characterized in that the strands to be connected to the sensors are formed as a braided wire, an insulating layer is provided on a surface of each of the strands in order to prevent mutual electric conduction of the strands, and a particular braided bundle is specified from among many braided bundles using a combination of colors of the insulating layers and a twist direction of the braided bundle that constitutes the braided wire as two indicators.

Advantageous Effects of the Invention

The application of the present invention enables the provision of the cable having a sufficiently small diameter and excellent flexibility even when many sensors are mounted thereon.

BRIEF DESCRIPTION OF THE DRAWINGS

FIG. 3 is a color table showing an example of color combinations for identifying braided bundles.

FIG. 4 is a schematic configuration diagram showing an example of a braider.

DESCRIPTION OF EMBODIMENTS

A braided cable 100 as an example of an embodiment of the present invention will be described below with reference to the accompanying drawings. Note that the sizes or dimensions of respective elements are partially depicted in a magnified manner for ease of comprehension of the drawings, and thus some parts do not necessarily coincide with those of an actual product. Note also that the drawings should be viewed in accordance with the orientation of reference signs. On the basis of such orientation, up, down, left, right, front, and back are defined.
(Configuration of Braided Cable)

The braided cable 100 is a cable that serves as a device for mounting sensors (not shown) such as temperature sensors.

Figure 1:
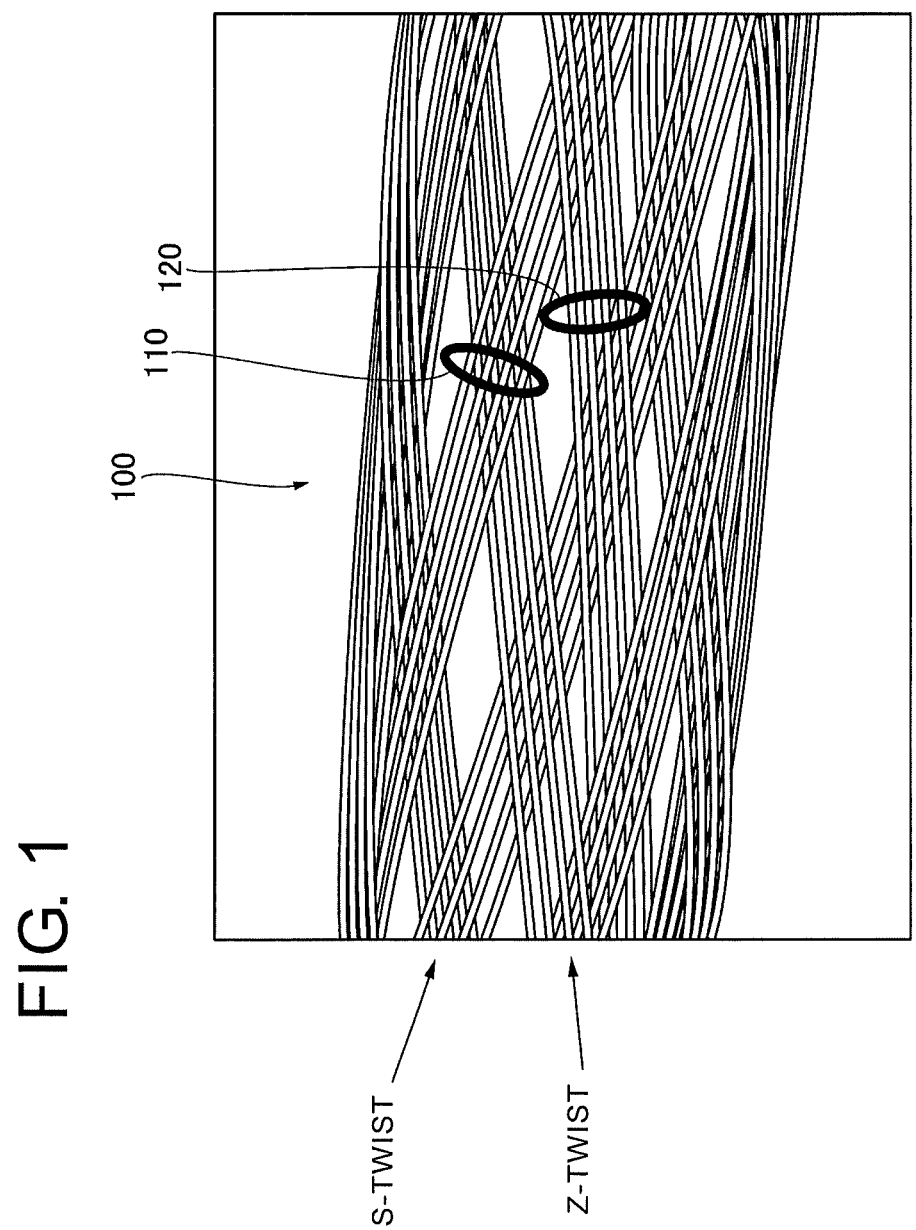
FIG. 1 is a partially-enlarged view of braided bundles in a braided cable showing an example of an embodiment of the present invention.
Figure 2:
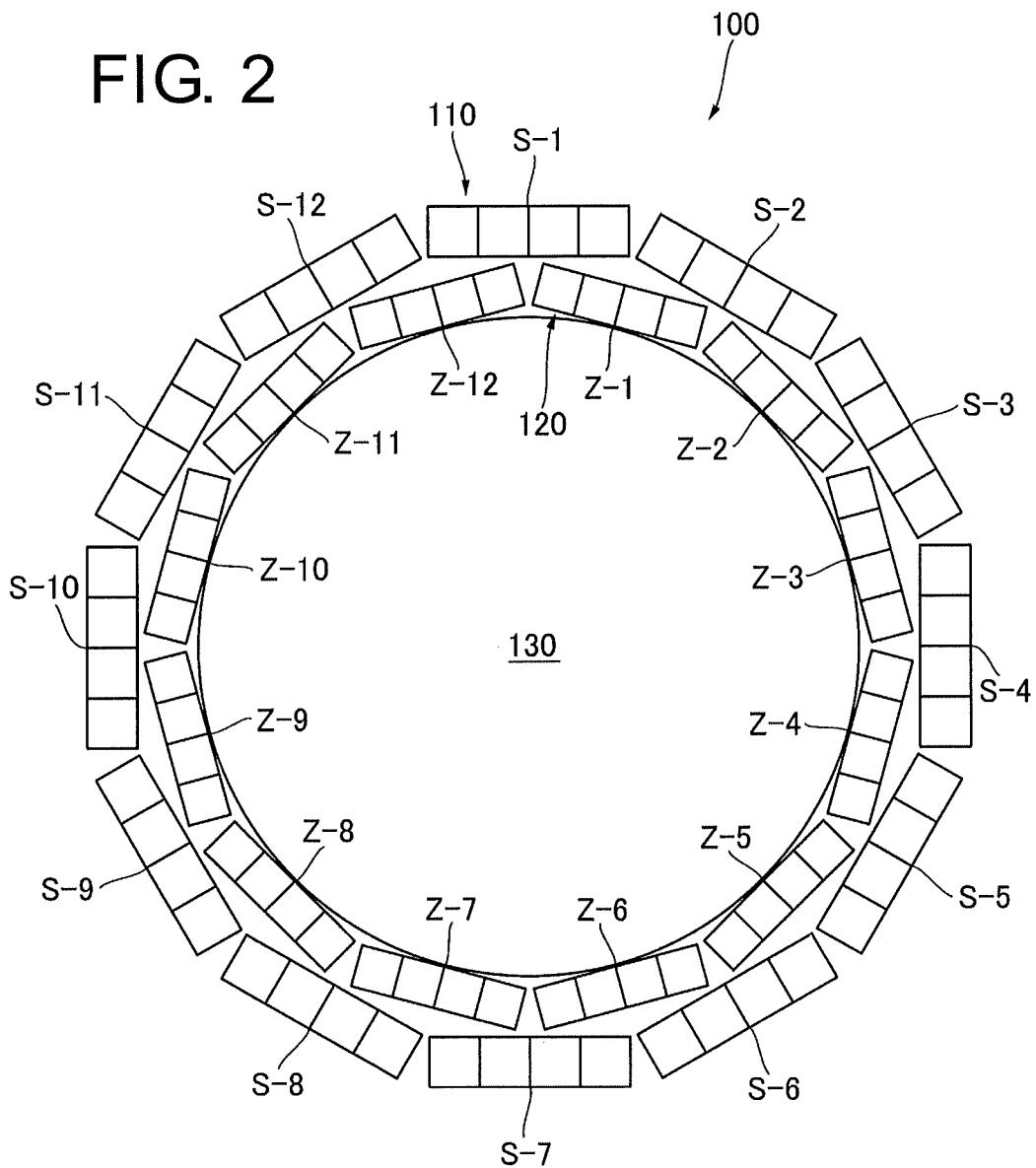
FIG. 2 is a schematic cross-sectional configuration diagram of the braided cable showing an example of an embodiment of the present invention.

As shown in FIGS. 1 and 2, braided bundles 110 and 120, in each of which four individually-insulated (e.g., enameled) strands form a single bundle, are braided around a core 130 to constitute the braided cable 100 in this embodiment. Any material having sufficient levels of strength and flexibility can be employed for the core 130. In some cases, no core 130 may be needed. Moreover, although not shown in the figures, a protective layer may be provided as needed on the outer periphery so as to cover the entire braided bundles 110 and 120.

In this specification, two twist directions of the braided bundles are expressed as an "S-twist" and a "Z-twist." In this embodiment, 12 S-twist braided bundles 110 (S-1 to S-12) and 12 Z-twist braided bundles 120 (Z-1 to Z-12), i.e., the total of 24 braided bundles, are braided. Therefore, the number of strands is 24×4=96. Assuming that two strands are connected to a single sensor, 48 temperature sensors can be mounted at the maximum. It is noted, just to be sure, that the number of strands that constitute a braided bundle and the number of braided bundles are shown by way of example, and those are, of course, not limited to the illustrated configuration.

The four strands that constitute each braided bundle 110 or 120 are all insulated, and further colored so as to be visually identified. In this embodiment, color combinations are defined according to a color table shown in FIG. 3. "A," "B," "C," and "D" in the table each represent some color. One example is "A→blue," "B→colorless," "C→green," and "D→red." While the four colors are herein employed, the number of colors is not limited thereto. In terms of realistic identification, however, immoderately using many colors makes the identification more difficult and increases the cost accordingly. Thus, it is desirable that the identification can be made with the least number of colors.

As described in the table shown in FIG. 3, in all the braided bundles 110 and 120 (S-1 to S-12 and Z-1 to Z-12), two strands have the same color. For example, two strands in S-1 have the "A" color, and two strands in Z-2 have the "D" color. Strands other than the two strands having the same color each have a different color and such a different color is different from the same color of the two strands in each braided bundle.

The color combinations of the S-twist braided bundles (S-1 to S-12) are the same as those of the Z-twist braided bundles (Z-1 to Z-12).
(Method of Identifying Braided Bundle in Braided Cable)

When a temperature sensor (not shown) is installed on the braided cable 100, the installation needs to be performed after accurately identifying which strand the temperature sensor is connected to.

In view of this, using the combination of the colors of the insulating layers in the strands and the twist direction, which are shown in the above configuration, as two indicators, a particular braided bundle 110 or 120 is selected first, and then a strand in the braided bundle is selected.

For example, the 24 braided bundles can be narrowed down to 12 braided bundles by observing its twist direction.

Thereafter, the 12 braided bundles can be narrowed down to three braided bundles by observing "what color two strands have (the color of identification wires)."

Once the braided bundles can be narrowed down to three, then a particular braided bundle can be identified on the basis of a combination of the other colors (the colors of the wiring strands in the table of FIG. 3).

Finally, once the particular braided bundle can be identified, particular two strands therein can be selected very easily.

As just described, according to the present invention, the strands to be connected to the sensors are formed as a braided wire, and the insulating layer is provided on the surface of each strand in order to prevent the mutual electric conduction of the strands. Using a combination of the colors of the insulating layers and a twist direction of the braided bundle 110 or 120 that constitutes the braided wire as two indicators, a particular braided bundle 110 or 120 can be specified from among the many braided bundles 110 and 120.

Such a configuration enables the reliable provision of a sufficient number of strands enough to accommodate many sensors, and also allows the cable 100 to have excellent flexibility specific to a braided wire. Furthermore, the braided wire has "twist directions." By additionally using such a "twist direction" as an indicator for identifying a braided bundle, the kinds of colors for the insulating layers can be reduced (48 sensors at the maximum can be mounted with the four colors and the 24 braided bundles as described in the above-described configuration, for example). This can achieve easy identification and reduced cost.

The combination of the colors of the insulating layers was configured so that the same color was assigned to insulating layers in at least two strands of a plurality of strands that constitute a braided bundle 110 or 120, colors of insulating layers in the other strands of the braided bundle 110 or 120 were different from each other, and the mutually-different colors were different from the color of the insulating layers in the above two strands.

As just described, the identification of a braided bundle can be facilitated by assigning the same color to insulating layers in at least two of the strands that constitute the braided bundle 110 or 120. More specifically, the many braided bundles 110 and 120 can be narrowed down to a considerably smaller number of braided bundles 110 or 120 by observing "what color two or more strands have in the braided bundle 110 or 120" in addition to its twist direction. The strands themselves are extremely thin wires, and a large number of such thin wires are braided to constitute a braided wire. Thus, when only a simple color combination is employed, it is difficult to identify even a particular braided bundle 110 or 120. However, by assigning the same color to at least two strands in the braided bundle 110 or 120, such a color becomes distinct in the braided bundle 110 or 120 as a whole and can be thus identified easily.

The number of the strands that constituted the braided bundle 110 or 120 was four, and the same color was assigned to insulating layers in two of those strands.

Even when the color combinations of the insulating layers include only four colors, such a configuration enables the identification of a considerable number of braided bundles as well as strands that constitute the braided bundles.

Combinations of the colors of the insulating layers for one twist direction are the same as those for the other twist direction.

Such a configuration can reduce the number of colors in the color combinations of the insulating layers, facilitate the identification, and thereby prevent identification errors from occurring.

The invention claimed is:

1. A braided cable to be connected to sensors for receiving signals from the sensors, the braided cable being characterized in that:
   strands to be connected to the sensors are formed as a braided wire bundle;
   an insulating layer is provided on a surface of each of the strands in order to prevent mutual electric conduction of the strands; and
   a particular braided wire bundle can be specified from among many braided wire bundles using, as two indicators, a combination of colors of the insulating layers and a twist direction of the braided wire bundle.

2. The braided cable according to claim 1, wherein the combination of the colors of the insulating layers is configured so that a same color is assigned to the insulating layers of at least two strands of a plurality of strands that constitute the particular braided wire bundle, and colors of the insulating layers in the other strands of the particular braided wire bundle are different from each other and are different from the color of the insulating layers of the at least two strands.

3. The braided cable according to claim 2, wherein a number of the strands that constitute the particular braided wire bundle is four, and a same color is assigned to the insulating layers of two of the strands.

4. The braided cable according to claim 1, wherein the combination of the colors of the insulating layers for one twist direction is the same as that for another twist direction.

5. An identification method of identifying, when many sensors are attached to a cable constituted by a plurality of strands, which one of the strands corresponds to a particular one of the sensors, a method of identifying a braided bundle in a braided cable being characterized in that:
   the strands to be connected to the sensors are formed as a braided wire bundle;
   an insulating layer is provided on a surface of each of the strands in order to prevent mutual electric conduction of the strands; and
   a particular braided wire bundle is specified from among many braided wire bundles using, as two indicators, a combination of colors of the insulating layers and a twist direction of the particular braided wire bundle.

* * * * *